United States Patent [19]

Maeda et al.

[11] Patent Number: 4,888,945
[45] Date of Patent: Dec. 26, 1989

[54] METHOD FOR QUALITY CONTROL OF TEXTURED YARN

[75] Inventors: Yoshiyasu Maeda, Yamatokooriyama; Yasuhiro Inoue, Settsu; Toshiyuki Uno, Kusatsu; Kazuyoshi Suzuki, Nara, all of Japan

[73] Assignee: Murata Kikai Kabushiki Kaisha, Kyoto, Japan

[21] Appl. No.: 173,354

[22] Filed: Mar. 25, 1988

[30] Foreign Application Priority Data

Apr. 3, 1987 [JP] Japan .................................. 62-82526
Apr. 14, 1987 [JP] Japan .................................. 62-91126
Apr. 14, 1987 [JP] Japan .................................. 62-91125
Apr. 22, 1987 [JP] Japan .................................. 62-99449
Apr. 22, 1987 [JP] Japan .................................. 62-99448
Sep. 10, 1987 [JP] Japan .................................. 62-227107

[51] Int. Cl.$^4$ .................... D01H 13/14; D01H 13/22; D01H 13/26
[52] U.S. Cl. .............................. 57/264; 57/80; 57/81
[58] Field of Search .................... 57/78, 80, 81, 264, 57/265, 268, 271, 352

[56] References Cited

U.S. PATENT DOCUMENTS

| 2,641,960 | 6/1953 | Strother | 57/265 X |
| 3,662,531 | 5/1972 | Carroll | 57/265 |
| 3,667,292 | 6/1972 | Hada | 57/265 X |
| 4,168,604 | 9/1979 | Mannhart | 57/265 X |
| 4,292,800 | 10/1981 | Werst | 57/265 X |
| 4,362,011 | 12/1982 | Kikuchi | 57/352 X |

FOREIGN PATENT DOCUMENTS 57-1611  1/1982  Japan .
62-90341 4/1987  Japan .

Primary Examiner—Donald Watkins
Attorney, Agent, or Firm—Spensley Horn Jubas & Lubitz

[57] ABSTRACT

A method for quality control of yarn for false twisters having a plurality of take-up motions, consisting of conducting quality measurement of yarn upon doffing by the take-up motions at a first point where the yarn is being twisted and at a second point where the yarn is being untwisted to provide readings of quality measurement by means of a quality measuring device.

26 Claims, 10 Drawing Sheets

FIG. 17
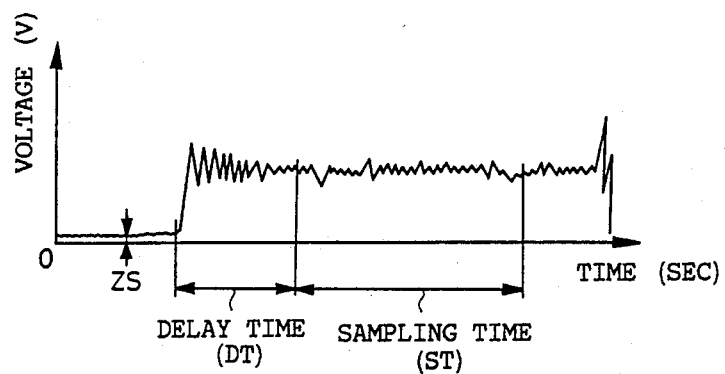
FIG. 18
| SPINDLE NO. | AVERAGE VALUE $\bar{x}$ (g) | | Cv (%) | | REJECT/ACCEPT |
|---|---|---|---|---|---|
| | T1 | T2 | T1 | T2 | |
| 1 | 30 | 26 | 2.0 | 6.5 | OK |
| 2 | 31 | 27 | 2.0 | 7.0 | OK |
| 3 | 30 | 28 | 2.0 | 7.4 | OK |
FIG. 19a  FIG. 19b
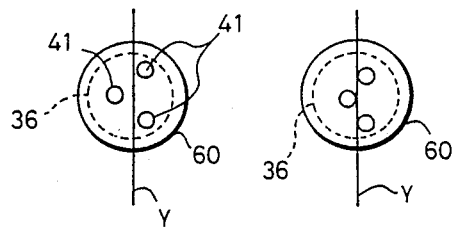

METHOD FOR QUALITY CONTROL OF TEXTURED YARN

FIELD OF THE INVENTION

The present invention relates to a method for quality control of textured yarn in false twisters.

RELATED ART STATEMENT

In a false twister as shown in FIG. 13, the filaments Y pulled from the feed package P1 in the creel stand a are passed sequentially through the first heater b, the cooling blade c, the false twister d and the second heater e while being twisted before they are taken up by the take-up packages P2 in the take-up motions f.

Conventionally, quality measurements of yarn on false twisters as to twisting conditions such as tension, yarn diameter, number of twists, and twisting temperature are conducted at different intervals of time and at different points of process. Such measurements may be carried out at a time interval altogether irrespective of or far much longer than the cycle of bobbin change or, as generally referred to as "doffing" when fully loaded packages in a take-up motion are replaced by unloaded bobbins. The points of process where measurement is taken may be the twisting zone 58 where the yarn Y is just about to pass a false twister d and the untwisting zone 59 where twisting by the false twister d is just completed.

However, because of the general design of false twisters d that they stand too large for the average height of the operator engaged in such quality measurement, the conventional methods have been found to demand very cumbursome labor and attention, requiring the use of a platform stand h. In addition, simultaneous measurement of twisting conditions at the twisting zone 58 and at the untwisting zone 59 of process have been proved very difficult. Furthermore, analysis of measured values on the spot or immediately upon measurement would be impossible for quick qualification.

In addition, because of the possible undesirable effects that measurement might have on the twisting process of yarn, as when the measurement is carried out on yarn as it is being wound by the take-up package P2, it has been usual practice to discard that package at the end of the measurement to obviate such effects. Moreover, in the case of measurement by a human quality auditor, the time periods between rounds of measurement have tended to be too lengthened for proper prevention of potential abnormality to the point that, because of trouble that has developed before the next round, all the yarn wound on every take-up package so far replaced since the last round of measurement might be defective.

OBJECT AND SUMMARY OF THE INVENTION

It is an object of the present invention to propose a method for achieving real time quality control in false twister without causing an undesirable effect on the textured yarn.

The present invention has been proposed to solve the above-mentioned problems. An embodiment of the present invention, which sets forth a method for quality control of yarn for false twisters having a plurality of take-up motions, consisting of the steps of conducting quality measurement of yarn upon doffing by the take-up motions at a first point where the yarn is being twisted and at a second point where the yarn is being untwisted to provide readings of quality measurement by means of a quality measuring device; and of analyzing a combination of the readings thus obtained at the first and second points in the quality control unit.

BRIEF DESCRIPTION OF THE DRAWING

FIG. 17 is curve plotted to show the relation between measuring time and voltage;

FIG. 18 is a table presenting results obtained by an analysis of tension readings; and FIGS. 19a and 19b are views to illustrate an opening and closing mechanism of the measuring instrument according to an embodiment of the present invention.

DETAILED DESCRIPTION OF PREFERRED EMBODIMENTS

The method for quality audit of textured yarn according to the present invention will be described in its most preferred embodiment in conjunction with the attached drawings. Prior to going in detail in the description of the invention, a false twister having a plurality of take-up motions, along with the doffing apparatus for false twisters proposed in former disclosure in Japanese patent provisional publication No. 62-90341 titled as "Method and Apparatus for doffing a Package for False Twisters" by the same applicant of the present invention, will first be explained with respect to FIG. 1.

Figure 1:
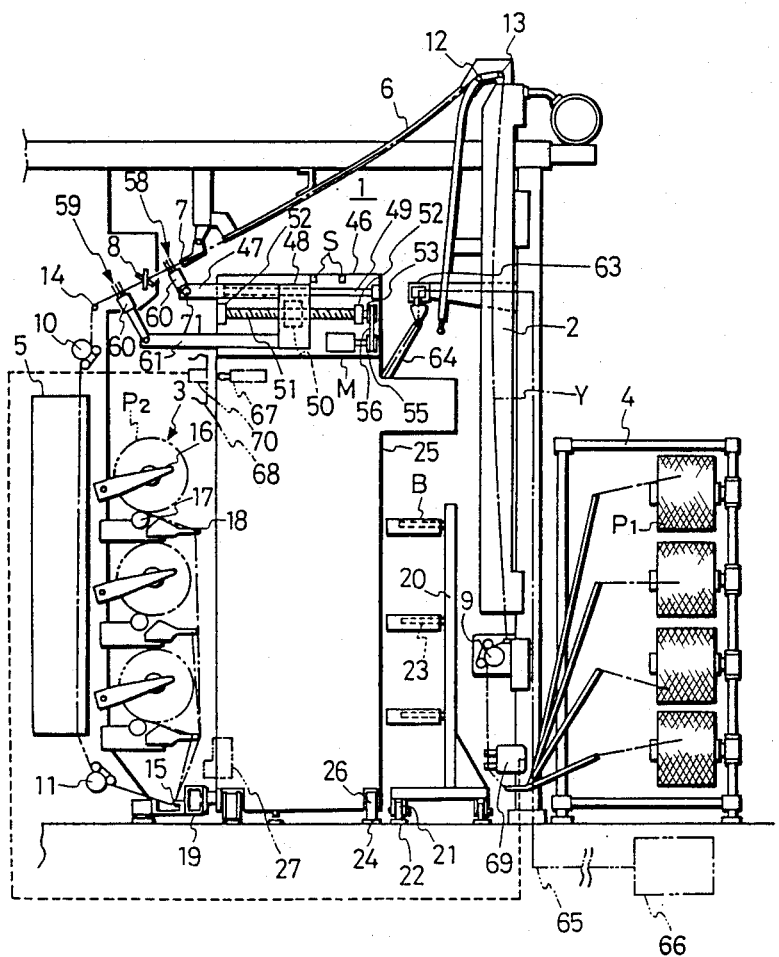
FIG. 1 is a view of a take-up motion in which a preferred embodiment of the method according to the present invention is employed.

FIG. 1 is a side view of a false twister. Along one side of the working space 1 of the twister is installed an elongate first heater 2. Opposite the first heater across the working space 1 is mounted a plurality of take-up motions 3. A creel 4 is located behind the first heater 2, which carries therein a plurality of feeding packages P1. A second heater 5 is located behind the take-up motions 3. A cooling plate 6, and a yarn guide 7, and a false twister 8 are mounted at a top portion of the working space 1. Also, a feed roller 9 is mounted below the first heater 2 while feed rollers 10 and 11 are mounted on upper and lower sides of the second heater 5.

The yarn Y pulled from the feed package P1, after leaving the first feed roller 9, is driven up through the first heater 2. The yarn is then caused to turn over around guide pins 12 and 13 to follow a downwardly inclined path along the cooling guide plate 6 into the false twister 8 via the yarn guide 7.

After leaving the false twister 8, the yarn Y is allowed to bend around a guide pin 14 to go downward, and then is passed around the second feed roller 10 before it is moved through the second heater 5. The yarn is then passed around the third feed roller 11 and then a yarn guide 15 before it is collected by the take-up motion 3 where the yarn is formed into a coil on a take-up package P2.

There may be 12 take-up packages P2 in a take-up motion 3, arranged in three vertical tiers each consisting of four units arrayed in the direction of view of the drawing. Each take-up package is supported by a cradle arm 16 which comprises of a rotatably driven friction roller 17, a yarn guide 18 adapted to guide the passage of yarn Y onto the package, and other components. A suction pipe 19 is provided at a lower end of the take-up motion 3 and is connected in air-flow communication to a blower, not shown.

A peg stand 20 is provided which is situated opposite the first heater 2 in the working space 1. The peg stand 20 is mounted on wheels 21 which rolls on rails 22 that are laid on ground such that the peg stand moves back and forth in the direction of view of FIG. 1. Stopper means, not shown, is provided to lock the peg stand 20 in fixed position opposite the take-up motion 3 for normal operation. In the side of the peg stand 20 facing the take-up motion 3 are provided 12 equally spaced pegs in three vertical tiers each consisting of four units arranged in horizontal direction. An empty bobbin B is mounted on each peg 23. A second set of rails 24 are installed on ground between the peg stand 20 and the take-up motion 3. A doffer 25 is provided which run back and forth on wheels 26 along the rails 24.

The doffer 25 has means, not shown, which, when the current take-up packages P2 are loaded in the take-up motion 3, cuts the yarn Y, dislodges the loaded take-up packages P2 from their respective cradle arms 16, pulls bobbins B from the peg stand 20 to fit onto the cradle arms 16, and sets the take-up packages P2 on the pegs 23.

A preferred embodiment of the method of quality audit employing quality measuring instruments will be described in accordance with the present invention with respect to FIGS. 4 through 7. The quality measuring instruments may comprise a yarn tension gauge 36, a yarn diameter gauge 37, a yarn twist gauge 38 for measuring the number of twists, and a yarn temperature gauge 39. These gauges 36, 37, 38, 39 employed may be any conventionally known types. Examples of measurement using them will be described.

For measuring the tension of yarn Y, the tension gauge 36 may be of a type carrying at a forward end thereof three probes 41 which are gently inserted into the yarn Y to determine its tension by measurement of inductance developed in the yarn. The thickness gauge 37 may measure the thickness of yarn Y by means of a denier sensor 42 that is mounted at a forward end of the gauge. To measure the number of twists in a yarn Y, the twist gauge 38 may use the action of a main disk 43, which is held in contact with the yarn Y, in relation to an auxiliary disk operatively connected to the main disk and mounted inside the gauge. The temperature gauge 39 may be designed to determine the temperature of yarn Y by means of a heat convection sensor that is installed in a measuring head 45 at a forward end of the gauge. Each of the gauges is supported on a mounting base 71 at one end thereof.

Gauges 36, 37, 38 and 39 may be properly removably installed at a forward end of a first arm portion 47 of a quality measurement unit 46 by means of their respective mounting bases 71 at a top portion of the doffer 25. Also, a second tension gauge 36 may be installed at a forward end of a second arm portion 61 of the quality measurement unit. The quality measurement unit 46 may also include a slidably disposed frame 48 to which the first and second arm portions are secured. The slidable frame 48 is supported on a drive arrangement of a slide bar 49 and a threaded rod 51 which moves the first and second arm portions 47 and 61 back and forth in a direction across the rails between the take-up motion 3 and the peg stand 20 through the frame. For this action, the frame 48 comprises a guide, not shown, slidably mounted on the slide bar 49 and a nut 50 thread-engaged around the threaded rod 51. The threaded rod 51 is rotatably supported by bearings 52, 52 mounted at both ends thereof for free rotation about its own axis. A pulley 53 is secured to one end of the threaded rod 51. A motor M is provided which carries on a output shaft thereof a pulley 55 that is drivingly connected to the pulley 53 by means of an endless drive belt 56 which transmits the torque from the motor to the threaded rod thereby moving the frame. Also, sensors S, S may be provided to detect the location of the frame 48 relative to the yarn so as to situate the first and second arm portions 47 and 61 in correct positions for measurements at the twisting zone 58 and untwisting zone 59, respectively.

Figure 2:
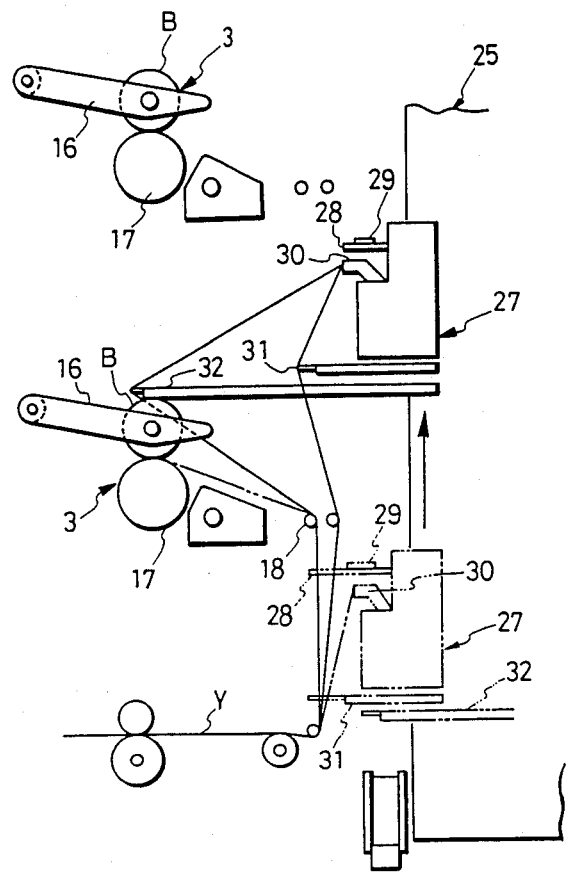
FIG. 2 is a view explaining how the yarn is hooked on the take-up motion of the FIG. 1 embodiment.
Figure 3:
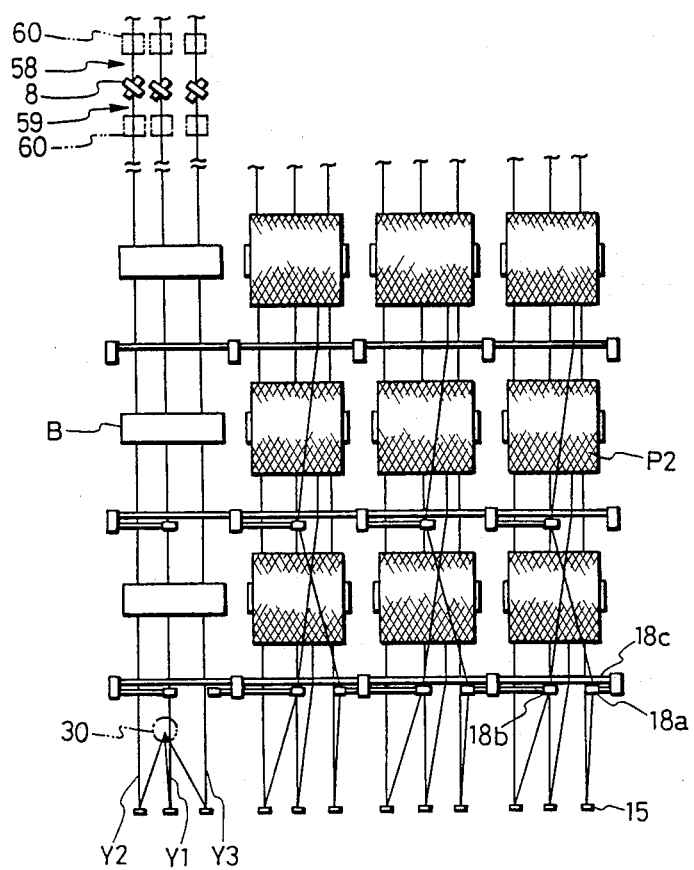
FIG. 3 is a schematic front view of a take-up motion on which a measurement by quality measuring instruments is explained.
Figure 4:
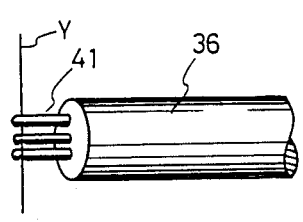
FIGS. 4 through 7 show examples of instruments used for quality measurement according to the method of the FIG. 1 embodiment.
Figure 6:
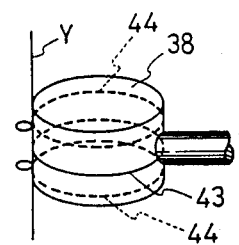
Figure 5:
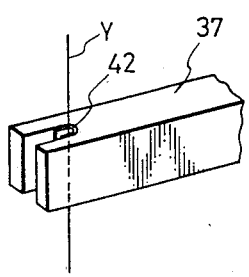
Figure 7:
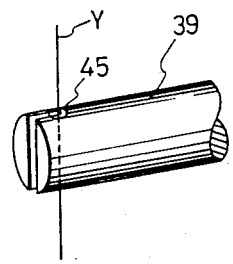

Referring then to FIGS. 1 through 3, the preferred embodiment of the present invention will be described. A yarn guide device 27 as shown in FIG. 2 is first operated to bring unloaded bobbins B to take up the yarn Y as they are mounted on their cradle arms 16 following the previous round of doffing. The yarn guide device 27 is movably disposed in the doffer 25 for vertical movement so that it can engage yarns in the three tiers of the take-up motion 3. Also, the yarn guide device 27 consists of a yarn handler 28 to handle the yarn Y at the end of the previous round of take-up, a cutter 29 to cut the yarn Y as it is handled by the yarn handler 28, a suction nozzle 30 which sucks in the cut end of the yarn, a distributor guide 31 to distribute the yarn Y between the three tiers, and a hooker 32 which moves the yarn from the suction nozzle 30 to the take-up motion 3 and hooks the yarn. In operation, the yarn guide device 27 has its yarn handler 28 to move the yarn Y toward the doffer 25 at the moment when a take-up package P2 is loaded with wound yarn. Whereupon the cutter 29 is activated to cut the yarn Y and the cut end of the yarn Y is caught by the suction nozzle 30. Then, yarn guide device 27 is moved vertical to the tier where an empty bobbin B is newly installed. The hooker arm 32 moves as shown in the drawing to hook the yarn Y at the take-up motion 3 after releasing it from the suction nozzle 30.

Referring to FIG. 3, quality measurement of the yarn is carried out when the yarn is being sucked by the suction nozzle 30, as illustrated in FIG. 3. Thus, any undesirable effect of measurement that might otherwise occur to a take-up passage would be limited to the yarn since it is being wound around an unloaded bobbin during the measurement. Means are provided to move a first quality measuring instrument 60, which is mounted at a forward end of the first arm portion 47 in the quality measurement unit 46, and a second quality measuring instrument 60, which is mounted at a forward end of the second arm portion of the unit, respectively to proper measuring position for determining the quality of the yarn Y either by contact or without contact at its points of measurement 58 and 59. This controlled movement of the quality measuring instruments 60 at the first and second arm portions 47 and 61 is achieved by moving the slide frame 48 to which the first and second arm portions are secured. The slide frame 48 is slided along the slide bar 49 toward the aforesaid points of measurement by the nut 50 which is advanced by rotation of the screw rod 51. The screw rod 51 is rotated by the pulley 53 secured thereto through the endless belt 56 which is driven by the motor M through the pulley 55 secured to the drive shaft of the motor. Also, the slide frame 48 may include a mechanism, not shown, to move the arm portions 47 and 61 to move from a first point of measurement where a first yarn Y2 is measured to the right in FIG. 3, at the end of the measurement, to a second point of measurement where a second yarn Y1 is measured, then to a third point for a third yarn Y3.

Then, how the measured data from the quality measuring instruments 60, 60 are sent to a quality control unit 66. In this particular embodiment, a power supply line comprised of a power supply line 63 and a power receiving arm 64 to supply electricity to the drive of the doffer 25. The measured data from the measuring instruments are sent to the quality control unit 66 through this power supply line, and are processed by analysis of readings of tension and frequency level for each take-up package and for each round of doffing. Data transmission may be done in any practical alternate manner such as wireless or use of a cable from a reel. Alternatively, the doffer may be equipped with a memory unit to store the data until they are processed at the end of each operation.

Figure 8:
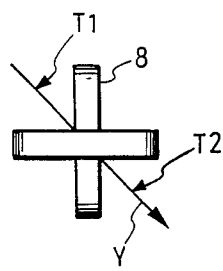
FIG. 8 is a schematic view explaining twisting and untwisting tensions.
Figure 9:
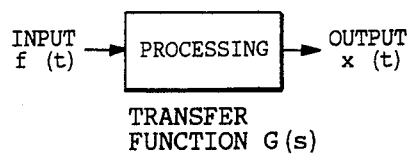
FIG. 9 is a view to illustrate a transfer function according to an embodiment of the present invention.

Referring now to FIGS. 8 through 12, the analytical processing of measured data 65 by the quality control unit 66 will be described. In this particular embodiment, one or more readings of the tension, thickness, number of twists, and temperature of the yarn measured at the twisting zone 58 are analyzed in combination of readings of the tension of the yarn measured at the untwisting zone 59. For example, when the yarn is measured with respect to tension at the twisting zone 58 and at the untwisting zone 59, respectively, the readings representing twisting tension T1 and untwisting tension T2 are obtained as transfer functions of input and output, as shown in FIGS. 8 and 9. Thus, transfer function G(s) is give by formula $$G(s) = X(s)/F(s)$$

where
F(s) is laplace transform for input f(t), and
X(s) is laplace transform for output X(t).

Figure 10:
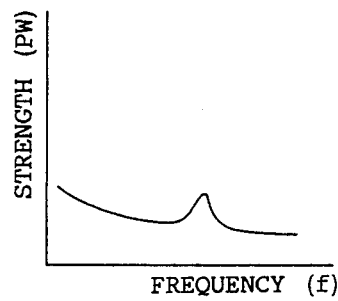
FIGS. 10 and 11 are diagrams plotted to show the relation of frequency and strength in measurement of a yarn according to an embodiment of the present invention.
Figure 11:
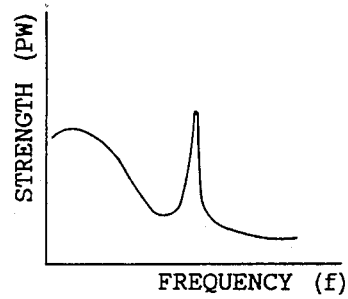

Furthermore, as shown in FIGS. 10 and 11 showing diagrams in which frequency (f) is taken on abscissa while strength (PW) is represented by ordinate, the curve in FIG. 10 runs to show low strength during normal condition. When something abnormal occurs in the twisting zone, the curve as shown in FIG. 11, shows high strength. In this manner, detection of abnormality is achieved.

Figure 12:
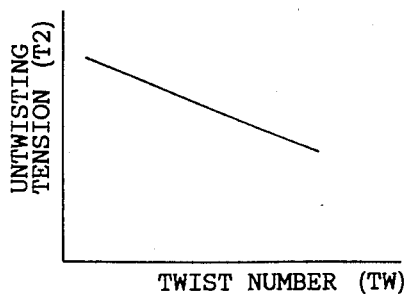
FIG. 12 is a diagram showing the relation of the number of twists in a yarn and untwisting tension developed in the yarn according to an embodiment of the FIG. 13 is a view showing an example of a conventional method for quality audit.
Figure 13:
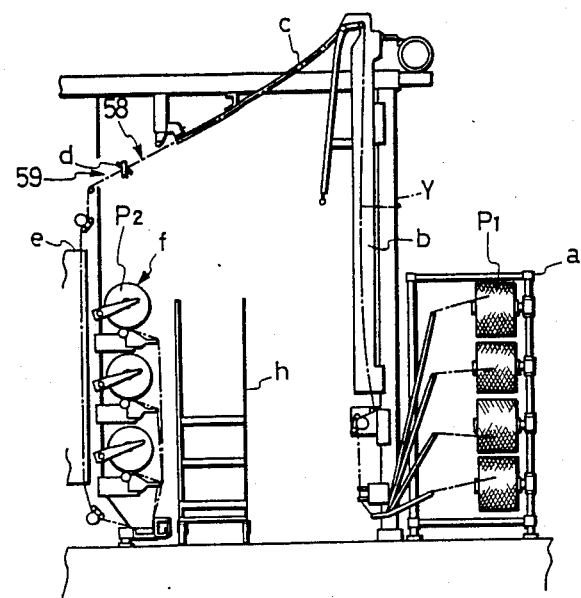

FIG. 12 shows plotting through a different combination of parameters in which the yarn is measured for tension both at the twisting zone 58 and at the untwisting zone 59. In the diagram shown, in which abscissa represents twisting tension (TW) while ordinate scaling untwisting tension (T2), the curve plotted is substantially direct line indicating that TW is inversely proportional to T2. Assuming this curve as indicating standard, for example, plottings of data are compared with this curve and how they deviate therefrom may be measured to determine abnormality. Alternatively, the number of twists in a yarn at the twisting zone 58 may be determined by measuring its tension at the untwisting zone 59 so that quality control data can be obtained as to abnormality of a yarn. In addition, more comprehensive quality control is possible through assessment and comparison of different combinations of plural parameters at given measurement points so as to insure high product quality at stable level during the twisting process.

Also, means are provided to cut a yarn during the twisting when any abnormality is detected according to the preferred embodiment of the present invention. This means consists of an actuator 67 mounted on the doffer 25 which is activated when the quality control unit 66 detects an abnormality in the results of its data analysis. Also, a button 70 is installed in a frame 68, which is mounted in the doffer on the side of the take-up motion 3, and is designed to send a signal to a cutter 69. When an abnormality is detected, the actuator 67 is activated to press the button 70 which in turn causes the cutter 69 to cut the yarn. Thus, take-up of a defective yarn is prevented, so that occurrences of defective packages are minimized. Moreover, as suspension of take-up action because of a defective yarn is prevented, machine efficiency is increased.

In this particular embodiment, the quality measuring instruments 60 are removably equipped on the forward ends of the arm portions 47 and 61 of the quality measurement unit 46 as they are required. However, this is a matter of choice and the measuring instruments 36, 37, 38 and 39 may be permanently mounted for measurement of the tension, diameter, number of twists, and temperature of yarn. In addition, they may be mounted on a single arm of the measurement unit for measurement either at the twisting zone or at the untwisting zone. Furthermore, it is to be noted that measurement should not be limited to the above-mentioned four parameters, but can be extended to other characteristics such as twisting speed and other operating conditions considered necessary for improved quality control of a yarn.

Figure 14:
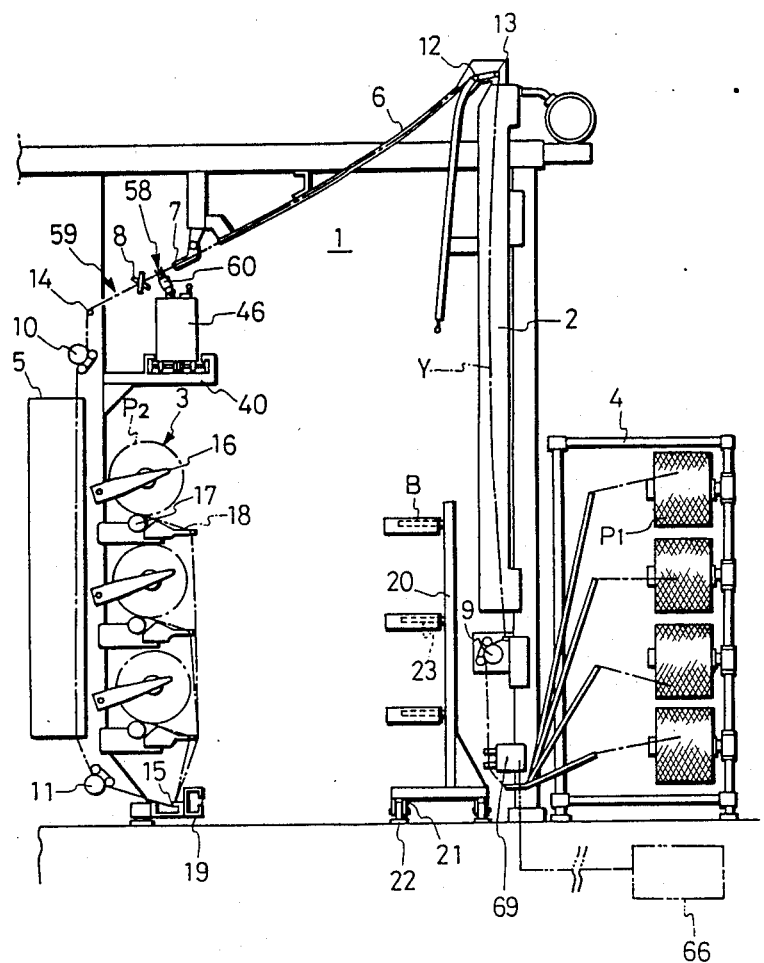
FIG. 14 is a front view to show another embodiment of a quality measuring instrument.
Figure 15:
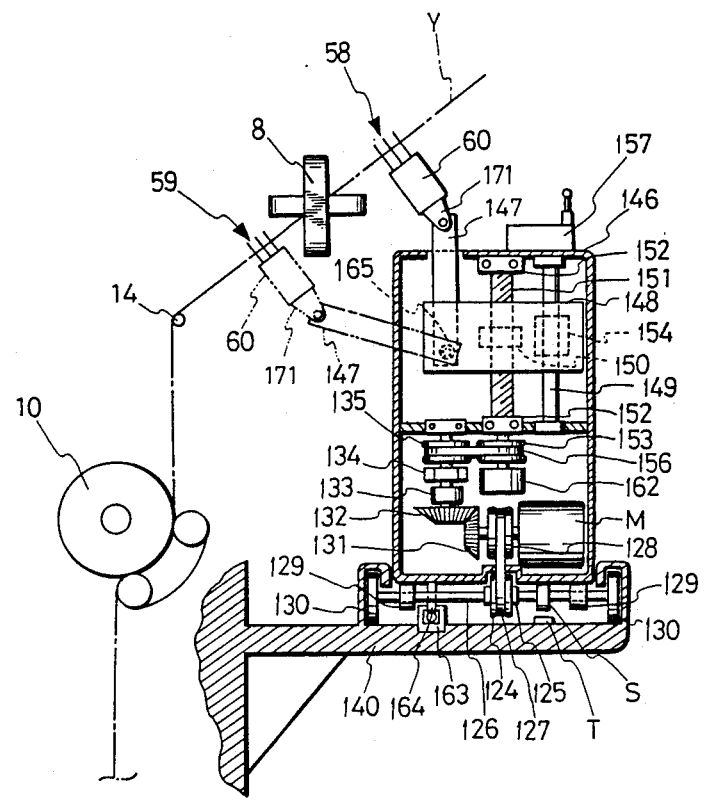
FIG. 15 is an enlarged view of FIG. 14 partly in section.

In the above-mentioned embodiment, the quality measuring instruments are mounted on the doffer. While, the quality measuring instruments may be provided on a travelling truck which travels along the side of the take-up motion of each spindle and the another embodiment will be described hereinafter. In FIGS. 14 and 15, a whole construction of a false twister is same as that of the above embodiment. At a top portion of the take-up motion 3 is provided a guide bracket 140 that extends in the direction of the horizontal arrangement of the motion (or in the direction of view to the drawing). A quality measurement unit 146 is mounted in the guide bracket 140 in such a manner that the quality measurement is freely movable therein along the side of the take-up motion.

Referring then to FIG. 15, the quality measurement unit 146 will be described in full detail. The quality measurement unit 146 is provided with a drive arrangement of a slide bar 149 and a screw rod 151 in which a slide frame 148 is freely reciprocally disposed for moving an arm 147 vertically. At a forward end of the arm is mounted a quality measuring instrument 60 for yarn quality measurement. The slide frame 148 comprises a guide member 154 that is slidably movably mounted around the slide bar 149 for movement therealong. Also, the slide frame has a nut member 150 mated with the screw rod 151 for movement therealong. The screw rod 151 is freely rotatably supported by bearings 152 at both ends thereof for rotation about its own axis. A pulley 153 is secured to one end of the screw rod 151 and is drivingly connected to another pulley 135 through an endless drive belt 156 that is passed around both pulleys. The pulley 153 is coupled to an encoder 162 which detects the rotational angle of the pulley. The pulley 135 is mounted on a shaft through which the pulley is connected via a reducer 134 and an electromagnetic clutch 133 to a bevel gear 132 secured to one end of the shaft. The bevel gear 132 is engaged in mesh with a second bevel gear 131 that is secured to one end of the drive shaft of a motor M for driving the pulley and belt arrangement. It is so designed that, when the electromagnetic clutch 133 is on, the rotation of the motor M is transmitted through the pulley and belt arrangement to the screw rod thereby driving the slide frame 148 up and forth. With the electromagnetic clutch 133 turned off, no rotation of the motor M is transmitted to turn the screw rod 151.

On the drive shaft of the motor M adjacent to the bevel gear 131 is mounted a pulley 128 adapted for driving the quality measurement unit 146. The pulley 128 is drivingly connected through an endless drive belt 127 to a forth pulley 124 that is mounted on a wheeled shaft 126. An electromagnetic clutch 125 is connected to this forth pulley. The shaft 126 is freely rotatably supported by bearings 129, 129 that are mounted at the rear bottom of the quality measurement unit 146. Also, the shaft 126 is carried by a pair of wheels 130, 130 secured to both ends thereof. At a front bottom of the quality control unit 146 is also provided with a similar shaft, not shown, carried by a pair of auxiliary wheels secured to both ends of the shaft and freely rotatably disposed. With this arrangement of the four wheels comprising the paired driving wheels 130, 130 and the paired driven wheels, the measurement unit 146 can be freely moved back and forth in the guide bracket 140. The electromagnetic clutch 125 is so designed that the rotation of the motor M is transmitted to the wheels 130, 130 through the shaft 126 thereby causing the measurement unit 146 to move, only when the electromagnetic clutch 125 is in the ON or closed position. When the electromagnetic clutch 125 is in the OFF or open position, no rotation of the motor M is transmitted and the measurement unit 146 remains standing still. Thus, selective operation of the two electromagnetic clutches 125 and 133 thus connected enables movement of the quality measurement unit by the incorporation of a single motor alone.

In this particular embodiment, the quality measurement unit 146 is connected to a power supply line 163 that runs in the guide bracket 140 in the direction of travel of the measurement unit 146 and provided to supply electricity to its drive system. In the bottom of the measurement unit 146 extends an elongate electricity receiving arm 164 that is built to keep sliding contact with the power line 163 as the measurement unit moves. It is to be noted that the supply of electricity to the drive system should not be limited to the above illustrated method, but various other known methods can be applied such as the use of a cable which can be unwound from or rewound onto a reel as the measurement unit moves. In an alternative way, the measurement unit 146 may be fed with electricity from a battery mounted thereon.

Also, sensor means S is provided in the bottom of the measurement unit 146 for detecting the location of the unit 146 in travel. An array of mark points T may be lined to scale distance in the surface of the guide bracket 140 for the sensor means S to determine the location of the measurement unit 146 when it moves over the mark points T. At a top portion of the measurement unit 146 is provided a transmitter/receiver 157. 171 designates a mounting member for each sensor 60.

The operation of this embodiment will be described.

Quality measurement of yarn may be carried out at any desired point of location or process time. When measurement is taken of yarn at the twisting zone 58 and at the untwisting zone 59 of twisting process, doing so during take-up of the yarn onto the take-up package tends to have an undesirable impact on the process of twisting particularly more likely at the twisting zone 58. Therefore, in this particular embodiment, measurement is taken at the time of doffing when the loaded packages P2 in the take-up motion 3 are replaced with empty bobbins B from the peg stand 20. When the quality measurement unit 146 receives a signal from the quality control unit 66 via the transmitter/ receiver 157, the motor M in the drive system transmits its rotation to the pulley 124 on the shaft 126 from the pulley 128 on the motor drive shaft via the endless drive belt 127, with the electromagnetic clutch 133 turned on. At this point, the electromagnetic clutch 133 for the arm section 147 is in its off position, the arm section is not connected to the motor for rotation. The wheels 130, 130 are thus driven by the shaft 126 moving the measurement unit 146 in the guide bracket 140. When the sensor S detects the particular mark point T for locating the measurement unit 146, the motor M is caused to stop, and hence the measurement unit 146. Whereupon the electromagnetic clutch 125 for the wheel shaft 126 is turned off, and the electromagnetic clutch 133 for the arm section 147 is subsequently turned on.

The motor M is then restarted driving the bevel gear 132 via the bevel gear 131 mounted on the motor shaft, causing the pulley 135 to rotate through the intermediary of the electromagnetic clutch 133 and the reducer 134. The rotation of the pulley 135 is translated to the pulley 135 mounted on the screw rod 151, causing the nut member 150 engaged around the screw rod 151 to drive the slide frame 148 along the slide bar 149. In this way, the arm section 147 mounted on the slide frame 148 is moved.

The measuring instrument 60 now must be pushed into a position where it can take measurement of the yarn Y, with which it may or may not be made to contact, at its twisting zone 58 or at its untwisting zone 59. To this aim, the encoder 162 is provided connected to the screw rod 151 at its one end to monitor the rotation of the motor M for control of the measuring instrument in conjunction with control means, not shown.

The arm section 147, at whose forward end is removably mounted the measuring instrument through the mounting base 171, is rotated about a pivot 165 at which the base section is rotatably disposed in the measurement unit 146.

The measured values from the quality measurement unit 60 are transmitted to the quality control unit 66 via the transmitter/receiver 157 which in turn analizes signalized values in strength or frequency to return quality control information on each of take-up packages. The power supply line connected to the drive system of the measurement unit 146 may be employed as signal transmission means for the quality control unit.

When an abnormality is detected in the results of analysis by the quality control unit 66, a cutter 69 is actuated by a signal from the quality control unit 66 to cut the yarn. Thus, no take-up of yarn onto a take-up would not be started and rejects as defective packages are reduced to a minimum.

Figure 16:
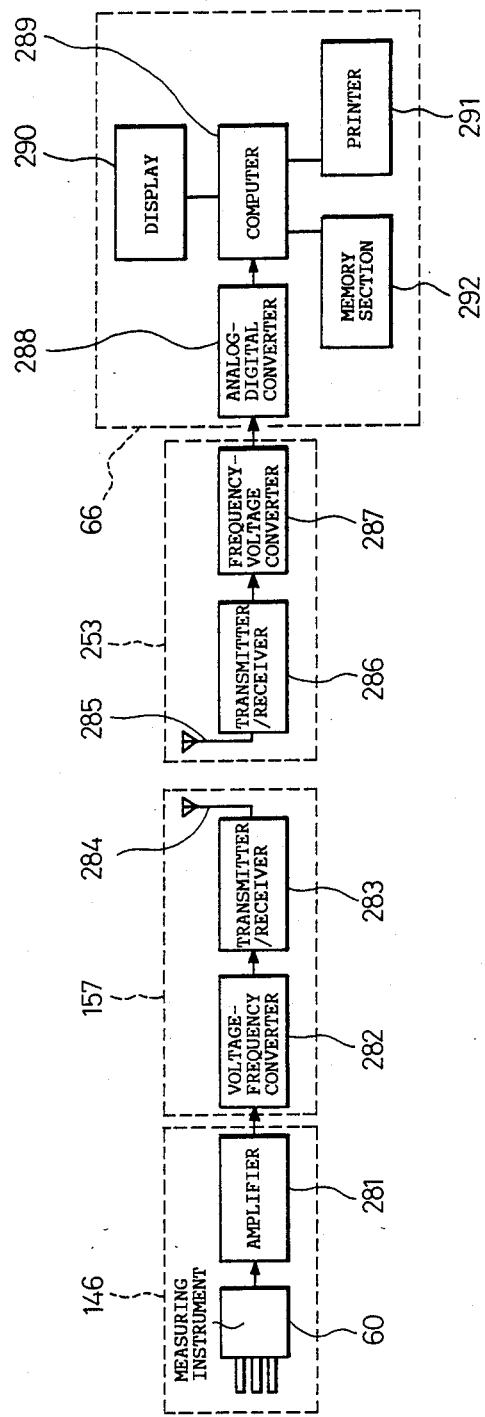
FIG. 16 is a block diagram showing the route of measured data transmission according to an embodiment of the present invention.

The transmission of measured data by wireless from the quality measurement unit will be described referring to FIGS. 16 to 19. FIG. 16 is a block diagram showing how the measured data is transmitted. The measured data (readings) by a quality measuring instrument 60, which may be equipped on the quality measurement unit for a given purpose, is passed as a voltage signal by an amplifier 281 to a transmitter/ receiver 157. The voltage signal indicative of the measured data input to the transmitter/receiver 157 is converted to a frequency signal by a voltage-frequency converter 282 which is modulated to a high frequency signal by the transmitter/receiver section 283 and then is sent out by wireless through an antenna 284.

The high frequency signal thus sent out is received by a second transmitter/receiver 253 through a second antenna 285 at a receiver and demodulated by the transmitter/receiver section 286 to a lower frequency signal which is then converted to a voltage signal by a frequency-voltage converter 287. The converted signal is then input to the quality control unit 66 and converted to a digital signal by an analog-digital converter 288 to be fed into a computer 289 for analytical processing.

Since measured data are transmitted by wireless, as described above, the method of this invention can dispense with cables so that the travelling truck or the doffer 25 carrying thereon a quality measurement unit 46, 146 is given greater freedom of movement. When a plurality of doffers 25 are operated, the number of quality measurement units 46, 146 and transmitter/ receiver units 157 installed on them would also be correspondingly plural. Even in such a case, a single quality control unit is used for centralized control, with each transmitter/receiver unit 157 being assigned with a different frequency range for wireless signal transmission so as to avoid confusion between the signals from different transmitter/receiver units 157.

Processing of the measurements sent by wireless by the quality measurement unit 46, 146 to the quality control unit will be described in conjunction with FIGS. 17 and 18.

When the measuring instrument 60 is not in contact with the yarn Y, as shown in FIG. 19a, the instrument must indicate that tension is 0 v. However, there may be a case where the measuring instrument is not set to 0 v when it should. Therefore, to avoid this problem, provision is made so that the value indicated by the instrument when in no operation is memorized as an initial set value (ZS), and the differential between this ZS and a value read by the measuring instrument 60 in measurement is recorded as a reading, as shown in FIG. 17. According to this method, it would be unnecessary to reset the measuring instrument 60 to indicate 0 v each time it is used for measurement. Thus, measurements can be completed in shorter periods of time.

In more detail, when the control unit receives at the outset of measurement a signal reflecting the measuring instrument in a position as shown in FIG. 19a, the signal is memorized as initial set value ZS. When measurement is in progress, with the instrument in a position as shown in FIG. 19b, the values indicated by the pointer of the instrument 60 might not represent real magnitude because of the vibratory motion of the pointer by inertia. Thus, the initial stages of measurement is regarded delay time DT while the later stages where the pointer gets stabilized being taken as sample time ST. Preferably, provision may be made to make delay time DT and sample time ST adjustable depending on the condition of measurement.

A computer 289 computes the average of the signal wave sampled out during sample time ST using the following formular:

$$\bar{x} = \Sigma xi/n$$

where
$\bar{x}$: average value
xi: measured values
n: number of measured values

Unless ZS is 0 v, ZS must be subtracted from the result (x) by the above formula to give the true value of average.

Next, the average (x) is converted from voltage (v) to tension (g).

Then, the following formula is employed to compute this converted value (CV) in percentage.

$$CV = \sigma \sqrt{\frac{1}{x}} = \sqrt{\sigma^2} \sqrt{\frac{1}{x}} = \frac{\sqrt{s/n}}{x}$$

where
$\sigma$: standard deviation
s: sum of squares of deviation $$s = \Sigma xi^2 - (\Sigma xi)^2/n$$

An example of output of average tention x (g) and CV by the above formulas on a display 290 or on a printer 291 is illustrated in FIG. 18. As shown, quality control data can be obtained for each individual take-up package in the spindles each time doffing is completed. In the table of the drawing, T1 presents values for the twisting zone 58 while T2 showing values for the untwisting zone 59. Values thus obtained are stored in the memory 292.

It will be clear from the above detailed descriptions that the quality control method according to an embodiment of the present invention permits quality measurement simultaneously at the twisting zone and at the untwisting zone of a yarn in a false twister, making it possible to achieve real time quality control through analysis of a combination of readings measured.

In addition, measurement is started immediately after the previous round of doffing is completed, without causing an undesirable effect on the finished yarn by measurement. Also, quality control data are obtained for each take-up package so that quality of take-up packages can be enhanced.

What is claimed is:

1. In a false twister having a plurality of take-up motions, a method for quality control of textured yarn comprising the steps of:

conducting quality measurement of yarn upon doffing in said take-up motions at a first point where said yarn is being twisted and a second point where said yarn is being untwisted to provide readings of quality measurement by means of a quality measuring device; and analyzing a combination of said readings at said first and second points in a quality control unit.

2. The method as claimed in claim 1, wherein said quality measurement of yarn is conducted with respect of one or more of the tension, thickness, number of twists and temperature of the yarn.

3. The method as claimed in claim 2, wherein data obtained by the quality measurement of yarn is transmitted by wireless to the quality control unit.

4. In a false twister having a plurality of take-up motions, a method for quality control of textured yarn comprising the steps of:

conducting quality measurement of yarn upon doffing in said take-up motions at a first point where said yarn is being twisted and a second point where said yarn is being untwisted to provide readings of quality measurement by means of a quality measuring device;

transmitting measured data by wireless to a quality control unit; and analyzing a combination of said readings at said first and second points in a quality control unit.

5. In a false twister having a plurality of take-up motions, a method for quality control of textured yarn comprising the steps of:

conducting quality measurement of yarn upon doffing in said take-up motions at a first point where said yarn is being twisted and a second point where said yarn is being untwisted to provide readings of quality measurement by means of a single quality measuring device.

6. An apparatus for quality control of textured yarn in a false twister having a plurality of take-up motions, where a single measuring device is provided to conduct a quality measurement of yarn for each spindle of the take-up motions, wherein a doffing truck which acts to exchange a full wound package on the take-up motions for an empty bobbin on a peg-stand is provided movably between the take-up motions and the peg-stand and said measuring device is located on the doffing truck so that the quality measurement of yarn is conducted upon doffing.

7. An apparatus for quality control of textured yarn in a false twister having a plurality of take-up motions, wherein a single measuring device is provided to conduct a quality measurement of yarn for each spindle of the take-up motions, wherein a doffing truck which acts to exchange a full wound package on the take-up motions for an empty bobbin on a peg-stand is provided movably between the take-up motions and the peg-stand and said measuring device is located on the doffing truck so that the quality measurement of yarn is conducted upon doffing, and wherein said measuring device comprises a first arm portion for measurement at a twisting zone, a second arm portion for measurement at an untwisting zone, said first and second arm portions having a quality measurement unit at a forward end thereof, respectively, and driving means for the first and second arm portions which includes a slidably disposed frame to which the first and second arm portions are secured, slide bar and a threaded rod to move the frame between the take-up motion and the peg stand, and a motor to rotate the threaded rod.

8. An apparatus for quality control of textured yarn in a false twister having a plurality of take-up motions, wherein a single measuring device is provided to conduct a quality measurement of yarn for each spindle of the take-up motions, wherein said measuring device is mounted on a traveling truck which travels adjacent the take-up motions of each spindle and includes an arm portion having a quality measuring instrument at a forward end thereof and pivoted for reciprocal movement about a shaft, a slide frame supporting the arm portion, a slide bar and a screw rod for up and down movement of the slide frame, and a motor operatively connected with both the screw rod and the traveling truck and being capable for driving the screw rod and the traveling truck.

9. The apparatus as claimed in claim 8, wherein an electromagnetic clutch is provided between the screw rod and the motor so that the slide frame is moved only when the electromagnetic clutch is in the closed position.

10. An apparatus for measuring yarn quality at a yarn twisting zone and a yarn untwisting zone of a false twister, the apparatus comprising:

a first yarn quality measuring instrument;

a second yarn quality measuring instrument;

transport means for moving the first and second yarn quality measuring instrument toward and away from the twisting and untwisting zones, respectively.

11. An apparatus as claimed in claim 10, wherein the transport means comprises:

a first support member arranged to support the first yarn quality measuring instrument;

a second support member arranged to support the second yarn quality measuring instrument; and a drive device operatively connected with the first and second support members.

12. An apparatus as claimed in claim 10, wherein the false twister includes a plurality of take-up motions, the apparatus further comprising:

a traveling truck movable adjacent the plurality of take-up motions;

wherein the first and second quality measuring instruments and the transport means are supported on the traveling truck.

13. An apparatus for measuring yarn quality at a yarn twisting zone and a yarn untwisting zone of a false twister, the apparatus comprising:

a yarn quality measuring instrument;

a movable support structure arranged to movably support the yarn quality measuring instrument; and drive means, operably connected with the movable support structure, for moving the yarn quality of measuring instrument toward and away from at least one of the yarn twisting zone and the yarn untwisting zone.

14. An apparatus as claimed in claim 13, wherein:

the movable support structure has a pivot point about which it is pivotable from a first position to a second position;
upon the movable support structure being pivoted to the first position, the drive means operates to drive the yarn quality measuring instrument toward and away from the yarn twisting zone;
upon the movable support structure being pivoted to the second position, the drive means operates to drive the yarn quality measuring instrument toward and away from the yarn untwisting zone.

15. An apparatus as claimed in claim 13, wherein the drive means comprises:
a rotatable threaded rod;
a rotational drive device operably connected with the threaded rod;
a movable nut threaded on the threaded rod and movable in the axial direction of the threaded rod as the threaded rod is rotated; and
a frame connected with the movable nut for movement with the movable nut;
wherein the movable support structure is connected with the frame for movement with the frame.

16. An apparatus as claimed in claim 15, wherein the false twister includes a plurality of take-up motions, the apparatus further comprising:
a travelling truck movable adjacent the plurality of take-up motions, the travelling truck having a drive wheel operatively connected with the drive device, the travelling truck further having a first clutch operatively connected to selectively engage and disengage the drive device with the drive wheel; and
a second clutch operatively connected to selectively engage and disengage the drive device with the threaded rod.

17. An apparatus as claimed in claim 13, wherein the false twister includes a plurality of take-up motions, the apparatus further comprising a travelling truck movable adjacent the plurality of take-up motions, the travelling truck having a drive wheel operatively connected with the drive means, the travelling truck further having a first clutch operatively connected to selectively engage and disengage the drive means with the drive wheel.

18. An apparatus as claimed in claim 17, further comprising sensing means for sensing the position of the travelling truck with respect to the plurality of take-up motions.

19. An apparatus as claimed in claim 13, wherein the false twister includes a plurality of take-up motions, the apparatus further comprising:
a travelling truck movable adjacent the plurality of take-up motions; and
sensing means for sensing the position of the travelling truck with respect to the take-up motions:
wherein the quality measuring instrument and the movable support structure are supported by the travelling truck.

20. An apparatus as claimed in claim 19, wherein the sensing means comprises:
a plurality of indicating members provided adjacent the plurality of take-up motions; and
detecting means for detecting the indicating members, the detecting means being provided on the travelling truck.

21. A method for quality control of yarn in a false twister having a plurality of twisting spindles and a truck movable adjacent the spindles, said method comprising the steps of:
supporting a first measuring instrument with a movable support structure;
supporting the movable support structure with the truck; and
moving the first measuring instrument with the movable support structure toward at least one of the twisting zones and the untwisting zone of a twisting spindle.

22. A method as claimed in claim 21, wherein said step of moving the first measuring instrument comprises the steps of:
moving the first measuring instrument with the movable support structure to the twisting zone; and
moving the first measuring instrument with the movable support structure to the untwisting zone.

23. A method as claimed in claim 21, further comprising the steps of:
supporting a second measuring instrument with the movable support structure;
moving the second measuring instrument with the movable support structure toward the other of the twisting and untwisting zones, with respect to the zone to which the first measuring instrument is moved.

24. A method as claimed in claim 23, further comprising the steps of:
moving the truck adjacent the spindles; and
performing the steps of moving the first and second measuring instruments for each of the spindles.

25. A method as claimed in claim 24, wherein the false twister also has a plurality of take-up motions and the truck includes a package doffing device operable to doff packages from the take-up motions, said method further comprising the steps of:
stopping the truck adjacent each spindle; and
doffing a package from each take-up motion.

26. A method as claimed in claim 21, further comprising the steps of:
moving the truck adjacent the spindles; and
performing the step of moving the first measuring instrument for each of the spindles.

* * * * *